(12) United States Patent
Fujimoto et al.

(10) Patent No.: US 9,867,667 B2
(45) Date of Patent: Jan. 16, 2018

(54) PLACEMENT APPARATUS

(71) Applicants:Canon U.S.A., Inc., Melville, NY (US); The Brigham and Women's Hospital Inc., Boston, MA (US)

(72) Inventors: Kosuke Fujimoto, Kawasaki (JP); Satoru Kitajima, Kawasaki (JP); Kemal Tuncali, Newton, MA (US)

(73) Assignees: Canon USA Inc., Melville, NY (US); The Brigham and Women's Hospital Inc., Boston, MA (US)

( * ) Notice: Subject to any disclaimer, the term of this patent is extended or adjusted under 35 U.S.C. 154(b) by 207 days.

(21) Appl. No.: 14/632,991

(22) Filed: Feb. 26, 2015

(65) Prior Publication Data

US 2015/0238266 A1 Aug. 27, 2015

Related U.S. Application Data

(60) Provisional application No. 61/945,543, filed on Feb. 27, 2014.

(51) Int. Cl.
*A61B 19/00* (2006.01)
*A61B 17/34* (2006.01)
*A61B 90/11* (2016.01)

(52) U.S. Cl.
CPC ............ *A61B 19/201* (2013.01); *A61B 90/11* (2016.02); *A61B 2017/3407* (2013.01); *A61B 2017/3409* (2013.01)

(58) Field of Classification Search
None
See application file for complete search history.

(56) References Cited

U.S. PATENT DOCUMENTS

| | | | |
|---|---|---|---|
| 4,841,967 | A | 6/1989 | Chang et al. |
| 4,955,891 | A | 9/1990 | Carol |
| 5,196,019 | A | 3/1993 | Davis et al. |
| 5,201,742 | A | 4/1993 | Hasson |
| 5,280,427 | A | 1/1994 | Magnusson et al. |
| 5,682,892 | A | 11/1997 | Selder |
| 5,797,835 | A | 8/1998 | Green |

(Continued)

FOREIGN PATENT DOCUMENTS

| | | |
|---|---|---|
| CA | 2784988 A1 | 2/2013 |
| EP | 2561821 A1 | 2/2013 |

(Continued)

OTHER PUBLICATIONS

Palmer, K., et al, "Development and evaluation of optical needle depth sensor for percutaneous diagnosis and therapies", Medical Imaging, Proc of SPIE, 2014, vol. 9036.

(Continued)

*Primary Examiner* — Brian T Gedeon
(74) *Attorney, Agent, or Firm* — Canon USA Inc., IP Division

(57) ABSTRACT

A positioning apparatus is provided that is configured to perform a biopsy or therapy support by puncture using a needle or other needle-shaped equipment. This positioning apparatus is exemplified by an apparatus that includes a first rotation member, a guide for guiding a needle or other needle-shaped equipment in a longitudinal direction, a second rotation member with a different rotation axis, and a friction applying unit configured to apply friction force to the first rotation member directly or indirectly and generates friction torque.

23 Claims, 16 Drawing Sheets

(56) References Cited

U.S. PATENT DOCUMENTS

| | | |
|---|---|---|
| 5,957,934 A | 9/1999 | Rapoport |
| 6,079,681 A | 6/2000 | Stern et al. |
| 6,119,032 A | 9/2000 | Martin et al. |
| 6,185,445 B1 | 2/2001 | Knüttel |
| 6,422,995 B2 | 7/2002 | Akiba |
| 6,676,669 B2 | 1/2004 | Charles et al. |
| 7,083,608 B2 | 8/2006 | Tomita |
| 7,187,104 B2 | 3/2007 | Yamamoto |
| 7,379,769 B2 | 5/2008 | Piron et al. |
| 7,636,596 B2 | 12/2009 | Solar |
| 7,766,878 B2 | 8/2010 | Tremaglio, Jr. et al. |
| 7,824,417 B2 | 11/2010 | Magnusson et al. |
| 8,241,301 B2 | 8/2012 | Zhang et al. |
| 8,308,740 B2 | 11/2012 | Tolley et al. |
| 8,340,743 B2 | 12/2012 | Jenkins et al. |
| 2001/0000940 A1 | 5/2001 | Maruyama |
| 2002/0019641 A1 | 2/2002 | Truwit |
| 2003/0107299 A1 | 6/2003 | Fujimoto |
| 2004/0064148 A1 | 4/2004 | Daum et al. |
| 2005/0216026 A1 | 9/2005 | Culbert |
| 2005/0261581 A1 | 11/2005 | Hughes et al. |
| 2006/0149147 A1 | 7/2006 | Yanof |
| 2006/0229641 A1 | 10/2006 | Gupta |
| 2007/0276407 A1 | 11/2007 | Vogele |
| 2008/0004481 A1 | 1/2008 | Bax et al. |
| 2008/0161829 A1 | 7/2008 | Kang |
| 2008/0167663 A1 | 7/2008 | De Mathelin |
| 2009/0079431 A1 | 3/2009 | Piferi et al. |
| 2009/0234369 A1 | 9/2009 | Bax et al. |
| 2010/0010505 A1 | 1/2010 | Herlihy |
| 2010/0082040 A1 | 4/2010 | Sahni |
| 2011/0126844 A1 | 6/2011 | Cinquin et al. |
| 2011/0190787 A1 | 8/2011 | Sahni |
| 2011/0237881 A1 | 9/2011 | Kunz |
| 2011/0251624 A1 | 10/2011 | Yi |
| 2012/0022368 A1 | 1/2012 | Brabrand et al. |
| 2013/0069651 A1 | 3/2013 | Lumiani |
| 2013/0345718 A1 | 12/2013 | Crawford et al. |
| 2014/0052154 A1 | 2/2014 | Griffiths et al. |
| 2014/0121675 A1 | 5/2014 | Bax et al. |
| 2014/0128881 A1 | 5/2014 | Tyc et al. |
| 2014/0128883 A1 | 5/2014 | Piron et al. |
| 2014/0200445 A1 | 7/2014 | Boezaart et al. |
| 2014/0275978 A1 | 9/2014 | Fujimoto et al. |
| 2014/0275979 A1 | 9/2014 | Fujimoto et al. |
| 2014/0336670 A1 | 11/2014 | Brabrand et al. |
| 2014/0350572 A1 | 11/2014 | Elhawary et al. |
| 2016/0074063 A1 | 3/2016 | Arimitsu et al. |
| 2017/0014200 A1 | 1/2017 | Onuma et al. |
| 2017/0030557 A1 | 2/2017 | Chen et al. |
| 2017/0071626 A1 | 3/2017 | Onuma et al. |

FOREIGN PATENT DOCUMENTS

| | | |
|---|---|---|
| JP | 2004320846 A | 11/2004 |
| JP | 2005083961 A | 3/2005 |
| JP | 2008237971 A | 10/2008 |
| JP | 2008264108 A | 11/2008 |
| WO | 2011082517 A1 | 7/2011 |
| WO | 2012178109 A1 | 12/2012 |
| WO | 2013084107 A2 | 6/2013 |
| WO | 2014152685 A1 | 9/2014 |
| WO | 2017/132505 A1 | 8/2017 |

OTHER PUBLICATIONS

Song, S.E., et al., "Design Evaluation of a Double Ring RCM Mechanism for Robotic Needle Guidance in MRI-guided Liver Interventions", International Conference on Intelligent Robots and Systems, Nov. 3-7, 2013, Tokyo, Japan.

Hata, H., et al.,"MRI-Compatible Manipulator With Remote-Center-of-Motion Control", J Magn Reson Imaging, May 2008, 27(5): 1130.

Koethe, Y., et al., "Accuracy and efficacy of percutaneous biopsy and ablation using robotic assistance under computed tomography guidance: a phantom study" Eur Radiol., 2013.

Maxio Brochure: Planning and Targeting for CT guided Procedures by Perfint.

Perfint, Inc Maxio Robot—Features http://www.perfinthealthcare.com/MaxioFeatures.asp Accessed Sep. 11, 2015.

Song, S., et al., "Biopsy Needle Artifact Localization in MRI-guided Robotic Transrectal Prostate Intervention," IEEE Transactions on Biomedical Engineering, Jul. 2012, vol. 59, No. 7.

Fischer, G. S.,et al. "MRI Guided Needle Insertion—Comparison of Four Technique", In Annual Scientific Conference of the Society of Interventional Radiology, 2006. (Abstract only).

U.S. Office Action issued in U.S. Appl. No. 13/837,806 dated Feb. 3, 2015.

U.S. Office Action issue in U.S. Appl. No. 13/836,708 dated Jun. 27, 2017.

U.S. Office Action issue in U.S. Appl. No. 13/836,708 dated Jan. 11, 2017.

U.S. Office Action issue in U.S. Appl. No. 14/799,021 dated Dec. 22, 2016.

PLACEMENT APPARATUS

CROSS-REFERENCE TO RELATED APPLICATIONS

This application claims priority from Provisional Application No. 61/945,543 filed 27 Feb. 2014, the disclosure of which is hereby incorporated by reference herein in its entirety.

THE NAMES OF THE PARTIES TO A JOINT RESEARCH AGREEMENT

The presently claimed invention was made by or on behalf of the below listed parties to a joint research agreement. The joint research agreement was in effect on or before the date the claimed invention was made and the claimed invention was made as a result of activities undertaken within the scope of the joint research agreement. The parties to the joint research agreement are CANON U.S.A., INC, and The Brigham and Women's Hospital, Inc.

BACKGROUND OF THE INVENTION

Field of the Invention

The present invention relates to a positioning apparatus configured to perform a biopsy or therapy support by puncture using needle-shaped equipment.

Description of the Related Art

Demands for low invasion medicine are growing for improvement of quality of life (QOL) of patients in medical science. There have been developed percutaneous puncture therapies, such as percutaneous puncture ablation therapy and percutaneous puncture cryotherapy, as low invasion therapies.

However, since a portion which is the puncture target is not directly viewable in percutaneous puncture therapies, a surgeon has to perform puncture based on medical images such as magnetic resonance imaging (MRI) or computed tomography (CT) or the like. However, when employing these medical imaging apparatuses, it is difficult for the surgeon to obtain images in real time. Employing a special MRI allows the surgeon to obtain images in real time. However, in this case, the surgeon has to perform work in a narrow space. In either case, it is difficult for the surgeon to accurately reach the target, and it takes time for surgery.

A mechanism configured to assist puncture work such as described in U.S. Patent No. 2011/0190787 has been proposed as surgery support using medical images such as MRI or CT or the like. According to U.S. Patent No. 2011/0190787, a marker attached to a device is recognized on a medical image to obtain the posture of the device. Next, based on this posture and the position of the puncture target, the direction of puncture is determined, to assist puncture work. According to this mechanism, the surgeon can insert needle-shaped equipment into a different puncture target position from the same insertion point, whereby external injury can be reduced. Also, this mechanism can be reduced in size, whereby a patient wearing this apparatus enter an existing medical imaging apparatus without removing this apparatus.

SUMMARY OF THE INVENTION

In recent years, in order to improve QOL, there has been demanded increase in accuracy of puncture position for realizing less invasive therapy.

A positioning apparatus according an embodiment of the present invention includes: a first rotation member having first rotation flexibility; a guide configured to guide needle-shaped medical equipment in a longitudinal direction of the needle-shaped medical equipment; a second rotation member, which is connected to the first rotation member, including the guide, and having second rotation flexibility, of which the rotation axis is not parallel to the rotation axis of the first rotation member; and a friction applying unit configured to apply friction force to the first rotation member directly or indirectly for causing the first rotation member to generate friction torque. The friction applying unit applies friction force to the first rotation member directly or indirectly so that the first rotation flexibility component of the friction torque of the first rotation member is greater than the first rotation flexibility component of friction torque to be generated base on the rotation of the second rotation member.

The positioning apparatus serving as a puncture support apparatus configured to support puncture work having two types of rotation flexibility includes the friction applying unit as a unit configured to suppress at least the rotation of one guide. Accordingly, the positioning apparatus can perform positioning for puncture with high precision, without interfering with operation of the other guide.

Further features of the present invention will become apparent from the following description of exemplary embodiments with reference to the attached drawings.

BRIEF DESCRIPTION OF THE DRAWINGS

Further objects, features and advantages of the present invention will become apparent from the following detailed description when taken in conjunction with the accompanying figures showing illustrative embodiments of the present invention.

In the following description, reference is made to the accompanying drawings which are illustrations of embodiments in which the disclosed invention may be practiced. It is to be understood, however, that those skilled in the art may develop other structural and functional modifications without departing from the novelty and scope of the instant disclosure.

DESCRIPTION OF THE EMBODIMENTS

Figure 1A:
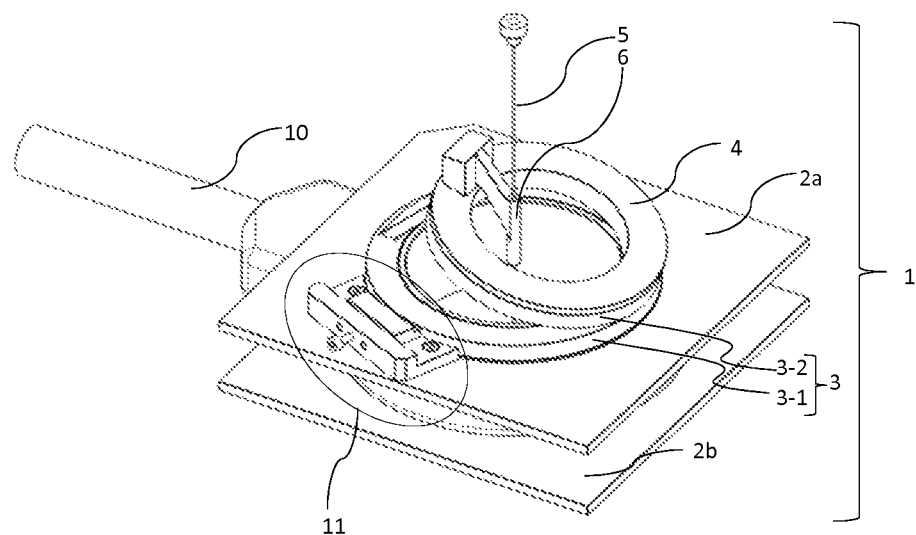
FIG. 1A is a perspective view of a puncture support apparatus according to a first embodiment.
Figure 1B:
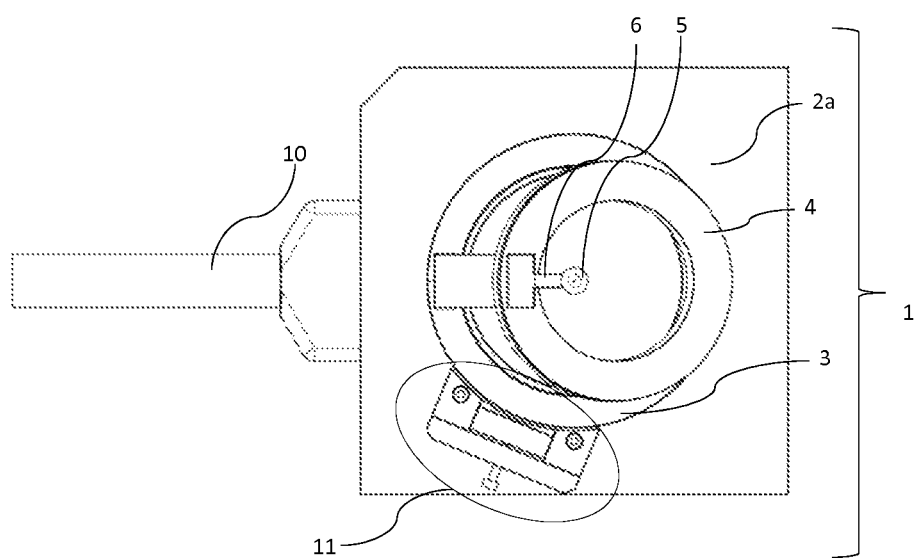
FIG. 1B is a top view of the puncture support apparatus according to the first embodiment.

The present assignee has been studying a puncture support apparatus (positioning apparatus) configured to secure space where a surgeon can access an insertion point and also to have improved rigidity using an apparatus in which two rotation mechanisms which two annular rotation members relatively drive are combined as illustrated in FIGS. 1A and 1B. The mechanism disclosed in the previously described U.S. Patent No. 2011/0190787 has a configuration in which a joint configuration and an arch portion are formed of a plate-shaped member. Therefore, this has a problem in that insufficient rigidity hinders realization of puncture with high precision.

On the other hand, since the mechanism as illustrated in FIGS. 1A and 1B supports inclined rotation mechanisms by being mutually connected, high rigidity is realized, and the problem in U.S. Patent No. 2011/0190787 can be solved. However, in the case of the configuration illustrated in FIGS. 1A and 1B, the rotation axes of the two rotation mechanisms are not orthogonal, so upon external force being applied to the upper rotation member for positioning of the upper rotation mechanism, the moment of force due to this external force includes a moment of force sufficient to rotate the lower rotation member. In the case that the operator applies external force to the upper rotation member for positioning of the upper rotation member, a moment of force exceeding the static friction torque of the rotation mechanism has to be added to the upper rotation member for the rotation mechanism starting relative rotation, and further, the dynamic friction torque of the rotation mechanism is applied to the upper rotation member during relative rotation. The moment of force obtained by multiplying this friction torque by the cosines of inclination angles of the rotation axes of the two rotation mechanisms is transmitted as torque for relatively rotating the lower rotation mechanism. Therefore, in the case that this torque exceeds the static friction torque of the lower rotation mechanism, the lower rotation mechanism is rotated, and moreover, it is difficult to rotate the upper rotation mechanism in accordance with a target. Accordingly, the mechanism such as in FIGS. 1A and 1B, from which a friction applying mechanism 11 has been excluded, has a problem in that the lower rotation mechanism turns even when performing positioning on the upper rotation member alone, and the obtained puncture position deviates from the desired puncture position. Though it is possible to cause the upper guide to turn while supporting the lower guide, when the operator is a surgeon, since operating the guide by both hands while handling another medical device increases medical procedures, so the burden on the surgeon or patient may increase.

Further, anything likely to be touched by the surgeon generally has to be sterilized. In the case of FIGS. 1A and 1B, since the surgeon may touch the surface of the apparatus, the surface of the apparatus has to be sterilized, or has to be covered with a sterilized sheet. In the case of performing positioning by relatively rotating the lower rotation mechanism alone, the surgeon has to apply external force to the lower rotation member by touching the lower rotation member, when the lower rotation member is covered with a sterilized sheet, the surgeon has to touch the lower rotation member through the sheet, so operability suffers. On the other hand, if the lower rotation mechanism can be rotated by applying external force to the upper rotation member protruding at the upper most portion, operations are easy, but since the moment of force for rotating the lower rotation mechanism includes a moment of force for rotating the upper rotation mechanism, when the friction torque of the upper rotation mechanism is small, the upper rotation mechanism is involuntarily rotated, and consequently, rotation of the lower rotation mechanism may be impeded.

Description will be made in detail regarding embodiments made in light of one of the above problems, or other problems.

First Embodiment

Figure 2A:
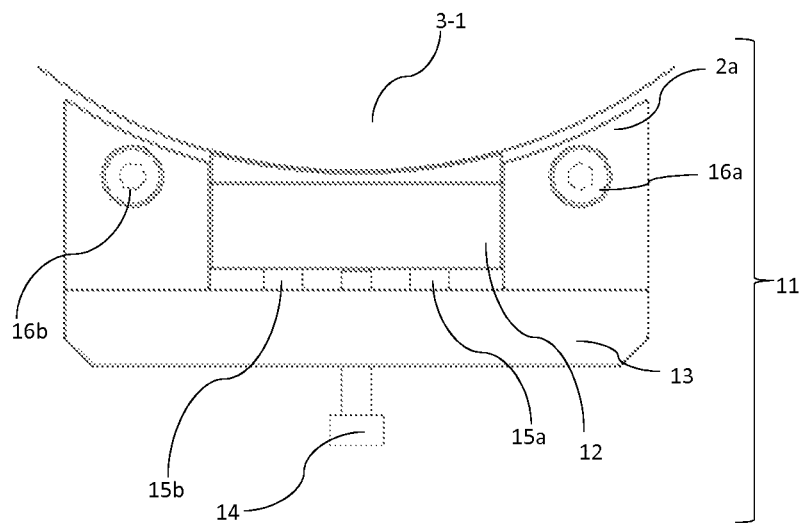
FIG. 2A is a diagram in which a first rotation member is set to a rotation-suppressed state by operating a friction applying mechanism according to the first embodiment.
Figure 2B:
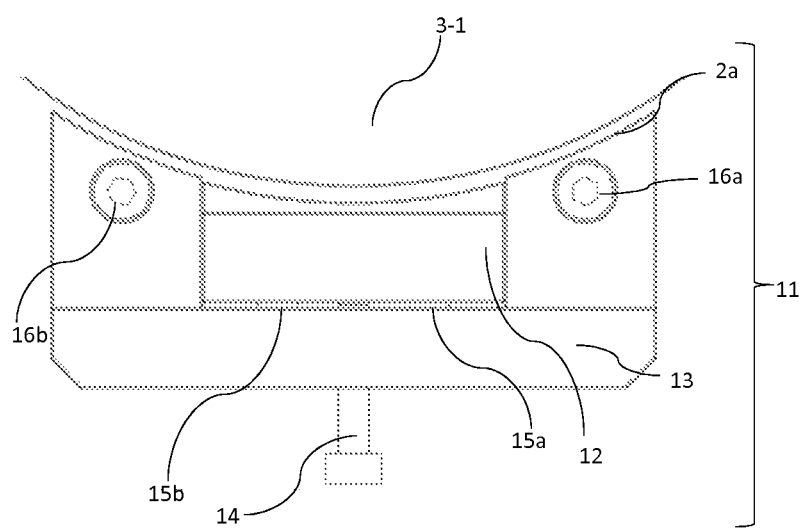
FIG. 2B is a diagram in which the first rotation member is set to a rotatable state by releasing the friction applying mechanism according to the first embodiment.
Figure 3:
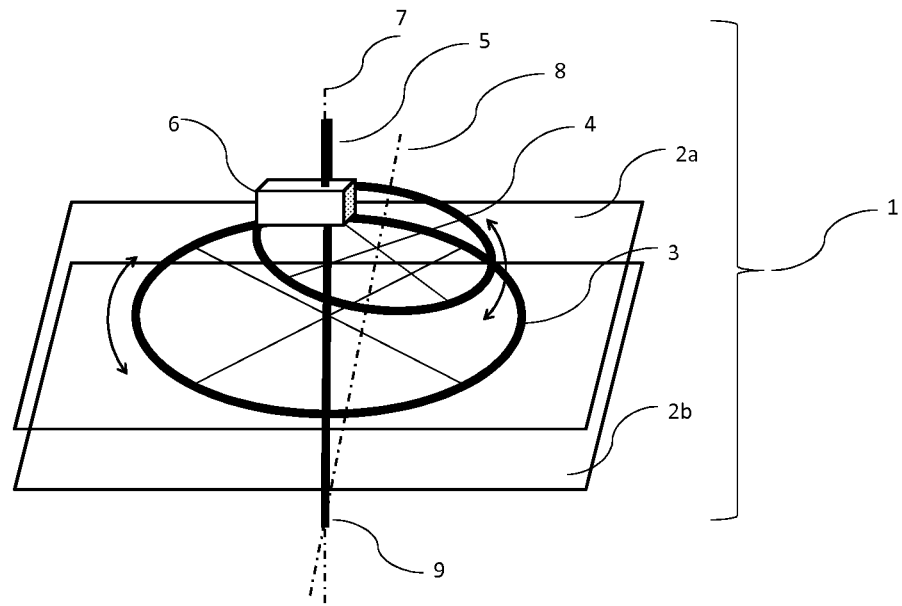
FIG. 3 is a schematic view in which the configuration of a movable unit at each rotation member is omitted.

A first embodiment of the present invention will be described with reference to FIGS. 1A to 3. FIG. 1A is a perspective view illustrating an external appearance of a puncture support apparatus 1 according to the first embodiment, and FIG. 1B is a top view of the puncture support apparatus 1. FIG. 3 is a schematic diagram representing the rotation and rotation axis of each rotation member while omitting the configuration of a rotation mechanism configured to relatively rotate each rotation member for simplification of description.

The puncture support apparatus 1 is configured of a base 2 made up of a first base 2a and a second base 2b, a first rotation member 3 rotatably disposed in the base 2, a second rotation member 4 disposed rotatably as to the first rotation member 3, a needle guide 6, which is disposed in the second rotation member 4, configured to guide a needle 5 to a predetermined direction, and the friction applying mechanism 11 configured to restrain the rotation of the first rotation member 3. The first rotation member 3 includes a first ring portion 3-1 and a second ring portion 3-2 inclined from the first ring portion 3-1. Note that the guide target by the needle guide 6 is not restricted to the needle 5. Another device may be used as a guide target as long as this is needle-shaped medical equipment.

First, the base 2b of the puncture support apparatus 1 is fixedly installed onto a puncture target using a fixing unit not illustrated in the drawings. A radiofrequency (RF) coil 10 is disposed between the bases 2a and 2b, and the puncture target is detected as an MRI image by the operation of an MRI and this RF coil 10. Also, the first ring portion 3-1 of the annular first rotation member 3 is rotatably attached to the base 2a, thereby configuring a lower rotation mechanism. Next, the annular second rotation member 4 is rotatably attached to the second ring portion 3-2 of the first rotation member 3, thereby configuring an upper rotation mechanism. In the case that the base 2a supporting the first rotation member 3 is used as a first base, the ring portion 3-1 making up part of the second rotation member will be referred to as a second base. As thus illustrated, the two upper and lower rotation mechanisms which are integrally connected, are configured.

Also, as illustrated in FIG. 3, the first rotation member 3 and second rotation member 4 are configured so that a rotation axis 8 with second rotational flexibility which represents the rotation center of the second rotation member 4 intersects a rotation axis 7 with first rotational flexibility which represents the rotation center of the first rotation member 3 at an intersection 9 positioned in the lower portion of the base 2b. That is to say, the rotation axis of the first rotation member 3 and the rotation axis of the second rotation member 4 are not parallel. The needle guide 6 is attached to the upper portion of the second rotation member 4. A through hole is provided to the needle guide 6, and the needle-shaped equipment 5 is fitted thereto, whereby the needle guide 6 guides the insertion direction of the equipment 5.

Also, a position detecting unit which is not illustrated is provided to the insides of the first rotation member 3 and second rotation member 4, and is capable of detecting the rotation angle of the corresponding rotation member. Examples of the position detecting unit include a detecting unit configured to optically or electrically detect a position such as an encoder or potentiometer or the like, and a detecting unit whereby the operator visually recognizes a scale provided to the rotation member. Also, a holder type detachably mountable as to the second rotation member 4 may be employed as the needle guide 6.

Combining the rotation operations of the first rotation member 3 and second rotation member 4 enables puncture from a desired angle to be performed without changing the position of the intersection 9 which is the puncture position.

In order to cause the first rotation member 3 and second rotation member 4 to perform rotation operation, the operator rotates the first rotation member 3 and second rotation member 4 by hand so as to apply torque on the rotation axis of each rotation member. The first rotation member 3 and base 2a, and the second rotation member 4 and first rotation member 3, are connected by providing a slide portion to each, as a rotation support configuration of the corresponding attachment portions in the present embodiment. A ball bearing and a needle bearing or the like may be employed as the rotation support configuration in addition to the slide portion. In the case of relatively moving the two rotation members by external force, friction force is generated at the rotation support unit by the friction of the slide portion, the rolling friction of a rolling member, or the like, which is multiplied by the rotation radius to generate friction torque of the rotation support unit. In the case of causing the second rotation member 4 to perform rotation operation, upon the operator applying rotation force to the second rotation member, torque obtained by multiplying the friction torque of the rotation support unit as to the first rotation member by the cosine of an angle made up of the rotation axes serves as torque for rotating the first rotation member. In the case that this torque exceeds the friction torque between the first rotation member 3 and base 2a, the first rotation member 3 is involuntarily rotated even when applying rotation torque to the second rotation member 4, so it is difficult to operate the second rotation member 4 to a desired angle.

The friction applying mechanism 11 configured to increase friction force to be applied between the first rotation member 3 and base 2a to restrain the rotation is disposed in the puncture support apparatus 1 according to the present embodiment. As illustrated in FIGS. 2A and 2B, the friction applying mechanism 11 is fixed to the base 2a supporting the first rotation member 3. FIG. 2A is a diagram in which the first rotation member 3 is set to a rotation-suppressed state by operating the friction applying mechanism 11, and FIG. 2B is a diagram in which the first rotation member 3 is set to a rotatable state by releasing the friction applying mechanism 11. The friction applying mechanism 11 is fixed to the top of the base 2a by bolts 16a and 16b, and is disposed on the outer diameter side in the radial direction of the first ring portion 3-1 of the first rotation member 3.

A friction member 12 is held by a friction member holding member 13, is movable in a direction orthogonal (radial direction) to the side of the first ring portion 3-1 of the first rotation member 3, and is inhibited from moving in the rotation direction (circumferential direction) of the first rotation member 3. Pins 15a and 15b are disposed in the friction member holding member 13. The pins 15a and 15b are inserted into a hole (not illustrated) provided to the side of the friction member 12. The friction member 12 is movable in the radial direction of the first ring portion 3-1, and is inhibited from moving in the circumferential direction and axial direction. The friction member 12 is suppressed from dropping from the puncture support apparatus 1 by disposing the above pins. A screw hole is provided to the side of the friction member holding member 13 in the radial direction of the first rotation member 3. Rotating the bolt 14 attached to the screw hole presses the friction member 12 against the side of the first rotation member 3 in the radial direction. According to this pressing force, friction force in the circumferential direction is applied between the friction member 12 and the side of the first ring portion 3-1 of the first rotation member 3, friction torque is applied to the first rotation member 3 as a moment of force multiplied by distance from the rotation center of the side of the first ring portion 3-1 of the first rotation member 3. Thus, friction torque according to the friction applying mechanism is added to friction torque of the rotation mechanism of the first rotation member 3 and base 2a to increase the friction torque of the first rotation member 3. Accordingly, the rotation of the first rotation member 3 can be suppressed by increasing the pressing force of the friction member such that the first rotation flexibility component of the friction torque of the first rotation member 3 increases so as to be greater than the first rotation flexibility component of the friction torque generated by the rotation of the second rotation member 4. The friction contact surface of the friction member 12 as to the first rotation member 3 has a shape generally agreeing with the curvature of the side in the radial direction of the first ring portion 3-1 of the first rotation member 3. In this case, generation of debris such as dust and so forth is suppressed by widening the friction contact surface to reduce friction.

The friction applying mechanism 11 is fixed to a fixed position of the base 2a, so visual recognition is good, and the operator can correctly operate the friction applying mechanism 11 without losing sight of the friction applying mechanism 11 during work. Also, after determining the puncture position, detaching the bolts 16a and 16b enables the friction applying mechanism 11 to be entirely detached, and the friction applying mechanism 11 can be suppressed from hindering the puncture work.

It is desirable that the first rotation member 3 rotates ±180 degrees. The friction applying mechanism 11 is disposed on the outer diameter side of the first ring portion 3-1 which is rotational symmetry as to the rotation axis of the first rotation member 3 in the present embodiment, thereby enabling the first rotation member 3 to be rotated ±180 degrees. However, the rotation angle is not restricted to this, the present invention may be applied even when the rotation angle is less than ±180 degrees. Therefore, the friction member 12 may be disposed in the upper portion in the axial direction of the first ring portion 3-1, and the rotation may be suppressed by sandwiching the first rotation member 3 between the friction member 12 and base 2a such as a disc brake.

As described above, according to the present embodiment, friction torque to be applied between the first rotation member 3 and base 2b is increased by the friction applying mechanism 11, thereby enabling the friction torque to exceed rotation torque to be applied to the first rotation member 3 by friction force between the second rotation member 4 and first rotation member 3. Thus, malfunction can be eliminated by suppressing the rotation of the first rotation member 3 due to the operation of the second rotation member 4. Specifically, after performing positioning by operating the first rotation member 3, the rotation is suppressed by the friction applying mechanism 11, and positioning of the second rotation member 4 is performed at the next process, whereby puncture positioning can be performed with high precision without rotating the first rotation member 3 at the time of positioning of the second rotation member 4.

Second Embodiment

Next, a second embodiment will be described with reference to FIGS. 4, 5A, and 5B. The second embodiment includes the same configurations as those in the first embodiment, so the same portions as the configurations in the first embodiment are denoted with the same reference numerals, description thereof will be omitted, and only different portions will be described.

Figure 4:
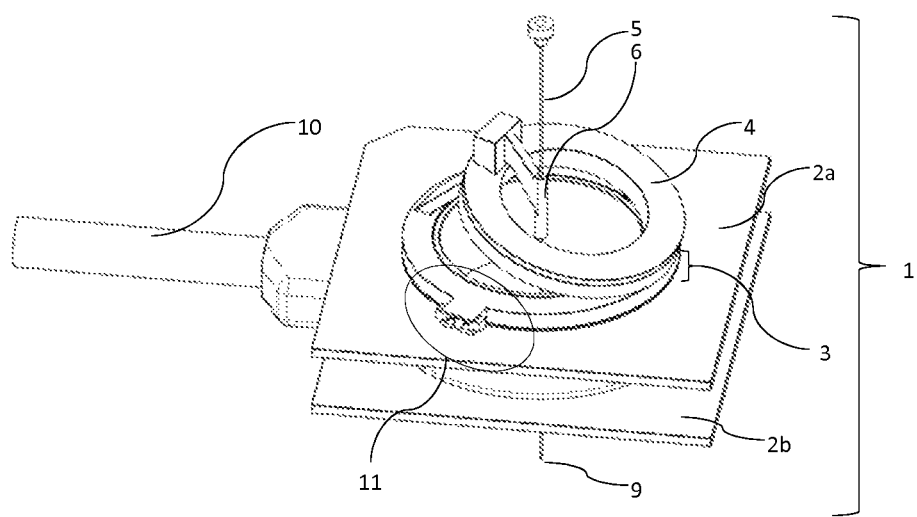
FIG. 4 is a perspective view of the puncture support apparatus according to a second embodiment.
Figure 5A:
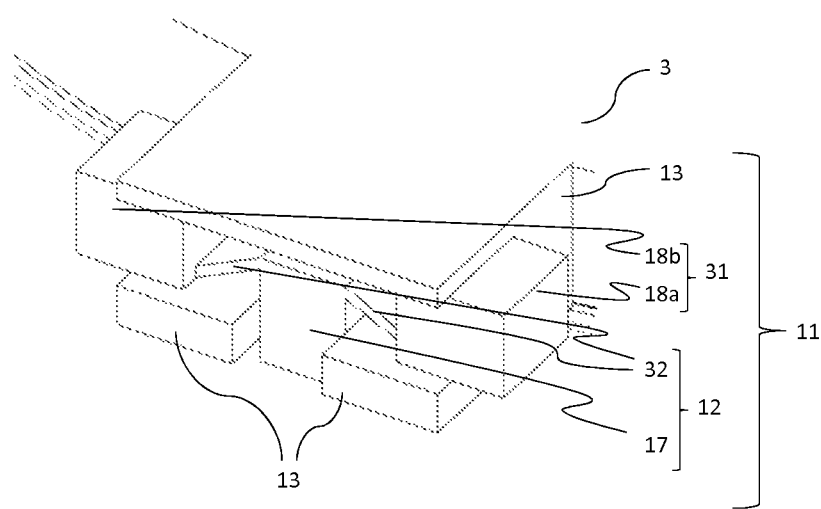
FIG. 5A is a detailed diagram of a friction applying mechanism according to the second embodiment.
Figure 5B:
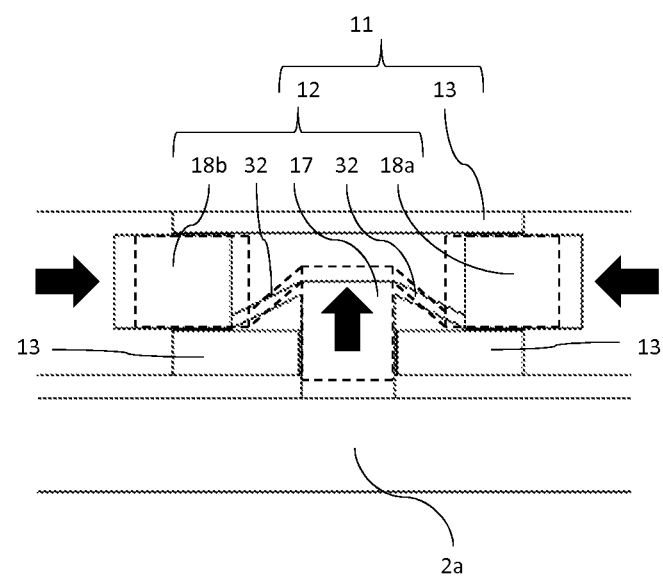
FIG. 5B is another detailed diagram of the friction applying mechanism according to the second embodiment.

FIG. 4 is a perspective view of a puncture support apparatus 1 according to the second embodiment. FIG. 5A illustrates a detailed diagram of a friction applying mechanism 11 according to the present embodiment. FIG. 5B illustrates a detailed diagram of the side of the friction applying mechanism 11 according to the present embodiment. A cover (not illustrated) to prevent the friction member 12 from falling off is attached to the friction applying mechanism 11.

The friction member 12 according to the present embodiment is provided by being fitted with the space of the friction member holding member 13 making up three plate shapes which protrude from the first rotation member 3. The friction member 12 is rotatably held integrally with the first rotation member 3. The friction member 12 is detachably mountable to the first rotation member 3 by being slid in a direction orthogonal to the rotation axis of the first rotation member 3.

The friction member 12 is configured of a friction portion 17, and the pressing portion thereof is configured of two buttons 18a and 18b, and a hinge portion 32 which is an inclined thin portion connected to the two buttons 18a and 18b. The hinge portion 32 is disposed between the two buttons 18a and 18b, and the friction portion 17. The buttons 18a and 18b, hinge portion 32, and friction portion 17 are formed in an integral manner. The friction portion 17 including the hinge portion 32 on both sides serves as an elastic member. More specifically, the inclined hinge portion 32 serving as pressing portions which are springs each having restoring force for restoring to the horizontal state, press the buttons 18a and 18b against the relatively upward friction member holding member 13, and press the friction portion 17 against the contact surface with the base 2a. The buttons 18a and 18b serve as operation units. In response to external operations, the positions of the buttons 18a and 18b serving as the operation units thereof are changed. For example, difference between the solid-line buttons 18a and 18b and the dotted-line buttons 18a and 18b in FIG. 5B is equivalent to this displacement. Pressure as to the base 2a disposed facing the friction portion 17 (elastic member) is increased or released according to this displacement.

The friction applying mechanism 11 is formed integrally with the first rotation member 3, and presses the friction portion 17 of the friction member 12 against the base 2a, thereby enabling the rotation of the first rotation member 3 to be suppressed. A mode has been described in the first embodiment in which the friction member 12 directly comes into contact with the first rotation member 3 and directly applies friction force thereto. On the other hand, according to the second embodiment, friction force is applied to the first rotation member 3 indirectly via the friction applying mechanism 11. The friction contact surface between the friction portion 17 and base 2a forms a flat surface. Since friction force according to the friction portion 17 coming into contact with the flat surface of the base 2a suppresses the rotation of the first rotation member 3, the wear of the contact surface between the friction portion 17 and base 2a is reduced to suppress generation of debris such as dust and so forth. There are provided the hinge-shaped buttons 18a and 18b in a direction orthogonal to the pressing direction of the friction portion 12 against the base 2 as units for releasing friction force. Upon these buttons being griped by the operator, the friction member 12 is deformed as illustrated by a dashed line in FIG. 5B to reduce or release friction force.

Since the first rotation member 3 and friction applying mechanism 11 are integrally formed, positioning of the first rotation member 3 is performed in a state griping the buttons 18a and 18b of the friction applying mechanism 11, and grip force is released after determination of the position, thereby enabling the rotation of the first rotation member 3 to be suppressed. Therefore, release of friction force, positioning, and fixing, can be performed as a series of operations by one hand, which improves workability.

The two buttons 18a and 18b are disposed in what we may call a twisted position in the present embodiment, where the axial line of force for gripping the two buttons 18a and 18b does not intersect the rotation axis of the first rotation member 3. However, the buttons 18a and 18b may be disposed in a direction where the axial line of force for gripping the two buttons 18a and 18b intersects the rotation axis of the first rotation member 3. Also, an arrangement may be made wherein one of the buttons 18a and 18b is fixed, and the other is movable, thereby enabling operations to be performed by one button. Also, the pressing direction of the friction portion 17 may be disposed in a direction intersecting the rotation axis of the first rotation member 3 instead of the direction parallel to the rotation axis of the first rotation member 3. Though the rotation suppression force of the first rotation member 3 is released by the operator grasping the buttons in the present embodiment, the rotation suppression of the first rotation member 3 may be performed by the operator grasping the buttons. Also, though the first rotation member 3 and friction applying mechanism 11 are integrally formed, these may be detachable.

Third Embodiment

A third embodiment includes the same configurations as those in the first embodiment, so the same portions as the configurations in the first embodiment are denoted with the same reference numerals, description thereof will be omitted, and only different portions will be described in the description of the third embodiment.

Figure 6:
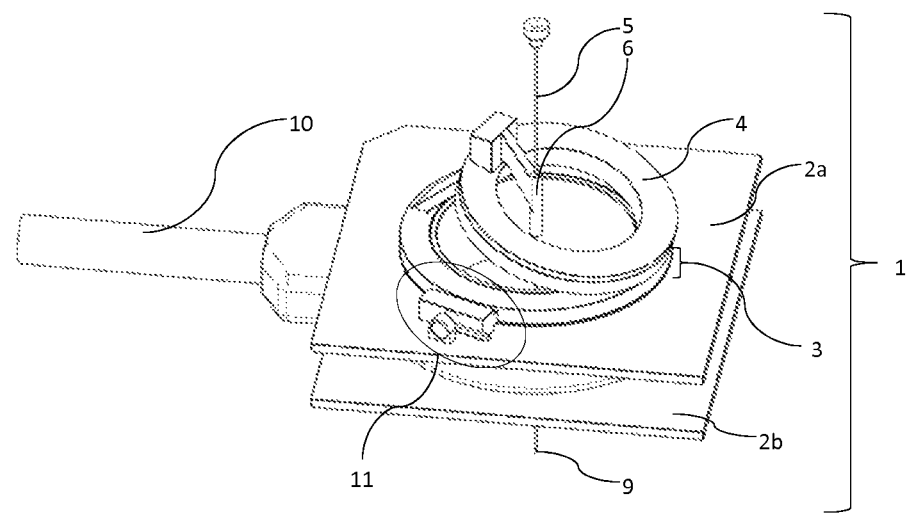
FIG. 6 is a perspective view of a puncture support apparatus according to a third embodiment.
Figure 7A:
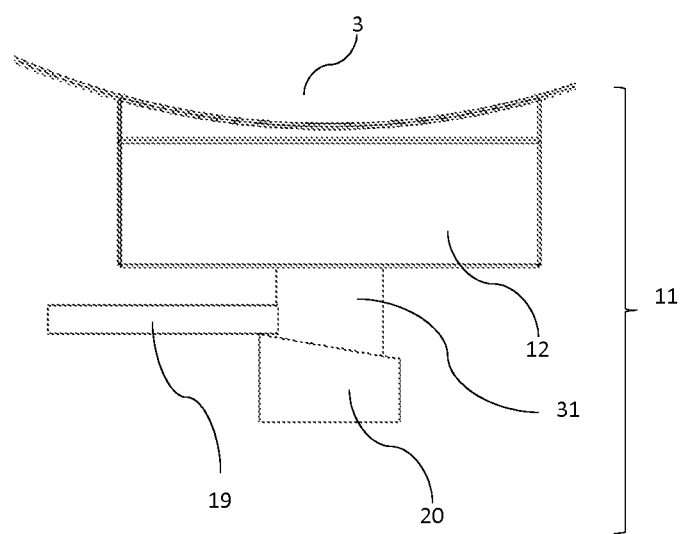
FIG. 7A is a diagram of a friction applying mechanism according to the third embodiment as viewed from the top.
Figure 7B:
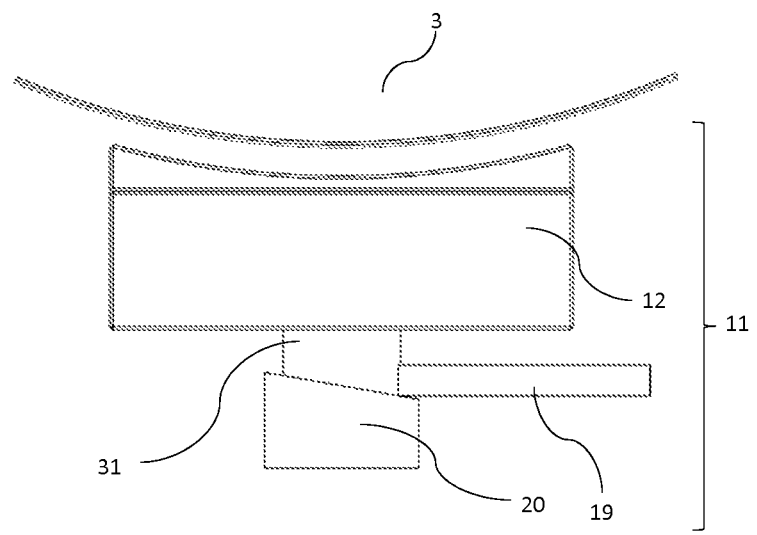
FIG. 7B is another diagram of the friction applying mechanism according to the third embodiment as viewed from the top.

FIG. 6 is a perspective view of a puncture support apparatus 1 according to the third embodiment. FIGS. 7A and 7B are diagrams of the friction applying mechanism 11 as viewed from the top. FIG. 7A is a diagram in which the operator operates the friction applying mechanism 11 to change the first rotation member 3 to a rotation-suppressed state, and FIG. 7B is a diagram in which the operator releases the friction applying mechanism 11 to change the first rotation member 3 to a rotatable state. The friction applying mechanism 11 is configured of a friction member 12, a pressing portion 31, a lever 19, and a holding member 20. The holding member 20 is formed integrally with the base 2a. The lever 19 has a prismatic shape. As illustrated in FIGS. 7A and 7B, it is understood that the pressing portion 31 is pressed via the lever 19, and the friction member 12 is accordingly moved along the axis of the pressing portion 31.

Figure 7C:
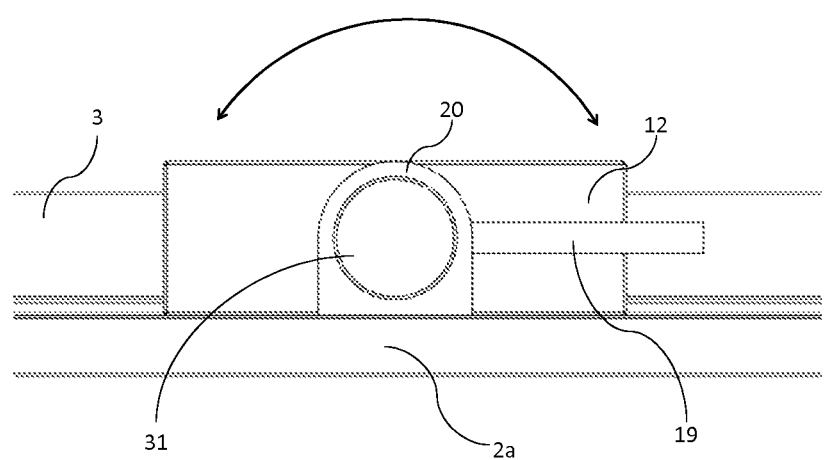
FIG. 7C is a diagram of the friction applying mechanism according to the third embodiment as viewed from the side.

FIG. 7C is a diagram of the friction applying mechanism 11 as viewed from the side. The lever 19 is rotatably attached to the friction member 12 and holding member 20. Upon the lever 19 being rotated in an arrow direction, the lever 19 moves along the inclination portion of the holding member 20, the friction member 12 presses the side of the first rotation member 3 to suppress the rotation thereof.

Figure 8A:
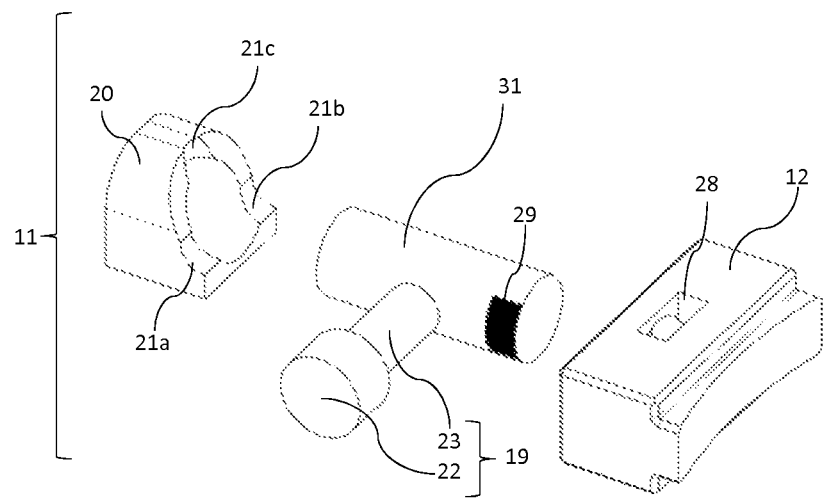
FIG. 8A is a perspective view of the friction applying mechanism according to the third embodiment.
Figure 8B:
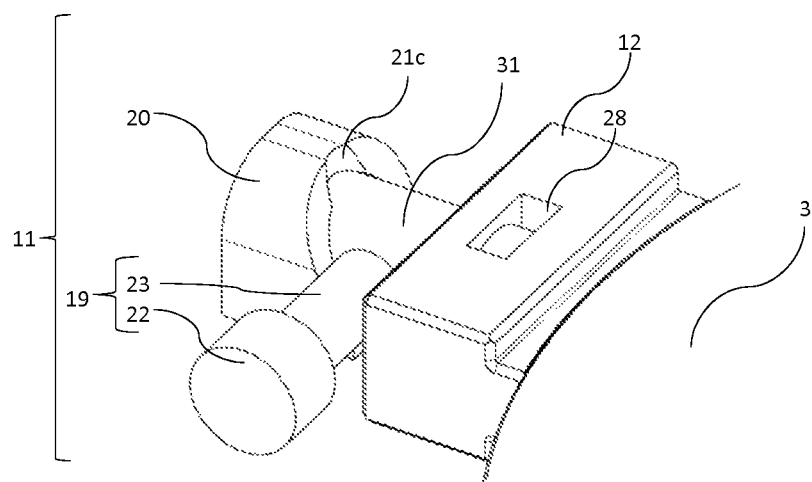
FIG. 8B is another perspective view of the friction applying mechanism according to the third embodiment.
Figure 8C:
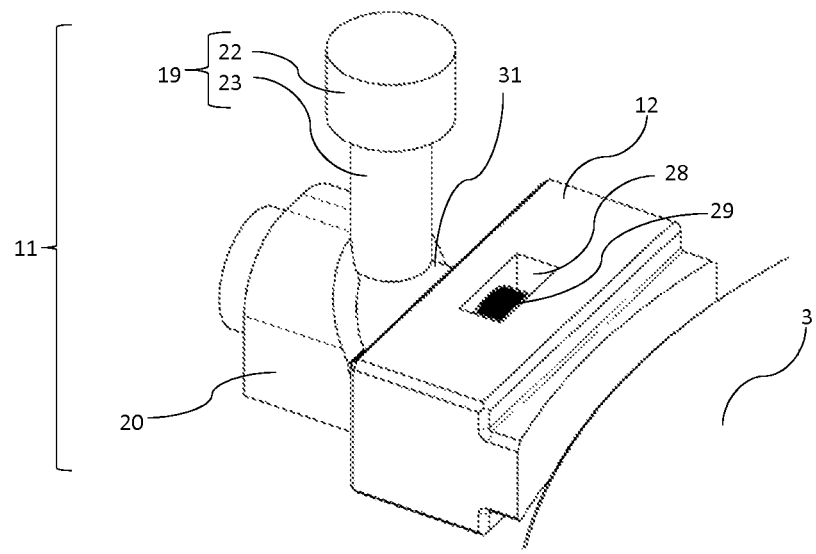
FIG. 8C is another perspective view of the friction applying mechanism according to the third embodiment.

Also, FIGS. 8A to 8C illustrate modifications of the friction applying mechanism 11 described in FIGS. 7A to 7C. FIG. 8A is an exploded perspective view of the friction applying mechanism 11, and FIG. 8B is a perspective view of the friction applying mechanism 11 in an assembly state. FIG. 8B is a diagram in which the operator operates the friction applying mechanism 11 to change the first rotation member 3 to a rotation-suppressed state, and FIG. 8C is a diagram in which the operator releases the friction applying mechanism 11 to change the first rotation member 3 to a rotatable state. It can be understood from these FIGS. 8A to 8C as well that the pressing portion 31 is pressed via the lever 19, and the friction member 12 is accordingly moved along the axis of the pressing portion 31.

Recesses 21a, 21b, and 21c are formed in the holding member 20. When rotating the lever 19 to the position of each recess, the lever 19 is fitted with the recess, thereby enabling the lever 19 to be temporarily stopped in a state in which external force is not applied to the lever 19, and accordingly, malfunction can be suppressed. FIG. 8C is a diagram illustrating a case where the lever 19 is fitted with the recess 21c. Also, when the lever 19 is positioned in the recesses 21a and 21b, the first rotation member 3 is in a rotation-suppressed state, and when the lever 19 is positioned in the recess 21c, the first rotation member 3 is in a rotatable state. Since a state in which the lever 19 is positioned generally perpendicular to the base 2a is the rotatable state of the first rotation member 3, the visual recognition of the lever 19 is improved, and the operator can readily visually recognize the operation state, whereby the operator can suppress malfunction. Further, a state in which the lever 19 is positioned generally perpendicular to the base 2a may be the rotation-suppressed state of the first rotation member 3, and the operator can also readily visually recognize the operation state. A columnar knob 22 is rotatably attached to the lever 19, which facilitates operations. Also, the shape of the knob 22 is not restricted to a cylindrical shape, and may be a globular shape, cylindrical shape, dome shape, or tapered shape. A cross-cut design to prevent slipping may be provided to the surface of the knob, or the knob may be formed integrally with the lever 19. A columnar roller 23 is attached between the lever 19 and holding member 20 in the present embodiment, so that the lever 19 rotates when moving along the inclined portion of the holding member 20, thereby enabling smooth operation.

A display unit 28 whereby the operator can visually recognize the side of the friction member 12 from an opening portion is provided to the friction member 12. A mark 29 corresponding to the position of the lever 19 is provided to the friction member 12. The operator can readily visually recognize whether the first rotation member 3 is a rotatable or rotation-suppressed state by confirming the mark 29 provided to the lever 19 from the display unit 28. In the case of FIG. 8C, the mark 29 serves as a notification part configured to notify that the friction member 12 is separated from the first rotation member 3. Also, an arrangement may be made wherein, regarding allocation of marks, the case in FIG. 8B allows the operator to visually recognize the mark 29, and the case in FIG. 8C allows the operator to have a visual state such as in the current FIG. 8B.

Also, in the cases of FIGS. 8A to 8C, though contact of the friction member 12 with the first rotation member 3, or separation of the friction member 12 from the first rotation member 3 has been described, as described in the second embodiment (FIGS. 5A and 5B), contact of the friction member 12 with the base 2a, or separation of the friction member 12 from the base 2a may be notified. Also, this configuration may be applied to not only the friction applying mechanism 11 corresponding to the first rotation member 3 but also the friction applying mechanism 11 corresponding to the second rotation member 4. Examples of the mark 29 include coating or a material with a color different from the colors of other portions, and a unit configured to emit light of a different color using a light-emitting diode (LED) or the like.

Figure 9A:
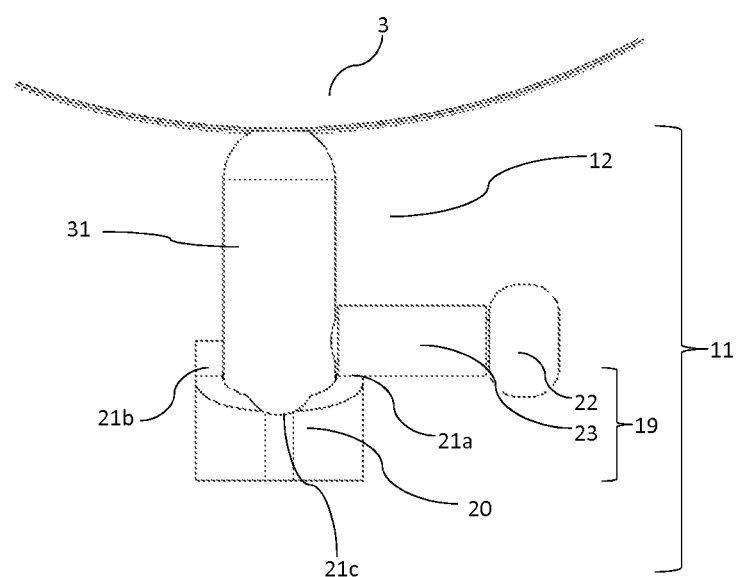
FIG. 9A is a diagram illustrating a modification of a friction contact portion.
Figure 9B:
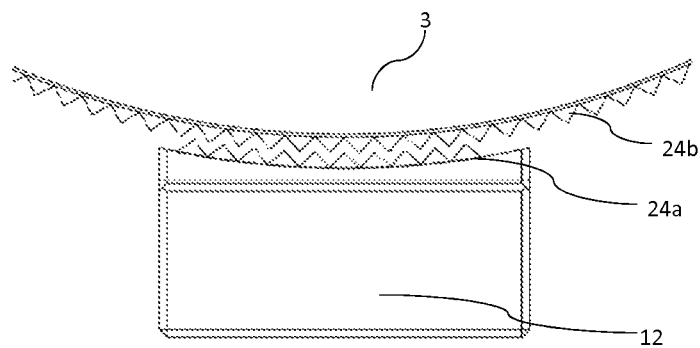
FIG. 9B is a diagram illustrating another modification of a friction contact portion

FIG. 9A is a diagram illustrating a state in which the external appearance of the friction applying mechanism 11 of the puncture support apparatus 1 according to a modification of the friction contact portion according to the third embodiment is viewed from above. In FIG. 9A, the lever 19 and friction member 12 are integrally formed. The friction contact portion of the friction member 12 has a spherical surface, and comes into contact with the first rotation member 3 at a point, whereby the rotation can solidly be suppressed. A generally spherical knob 22 is rotatably attached to the lever 19. FIG. 9B is yet another modification of the friction contact portion according to the third embodiment in which multiple raised and recessed portions 24b are provided to the side of the first rotation member 3 which is a rotation member with the friction contact surface of the friction member 12 to which multiple raised and recessed portions 24a are provided, whereby the rotation can solidly be suppressed. The contact surface of the first rotation member 3 may be a flat surface without any such raised and recessed portions. The form is not restricted to the form in which raised and recessed portions are engaged as illustrated in FIGS. 11A to 11C, and friction force may be increased by providing an irregular unevenness to the surface of the contact surface.

Figure 10:
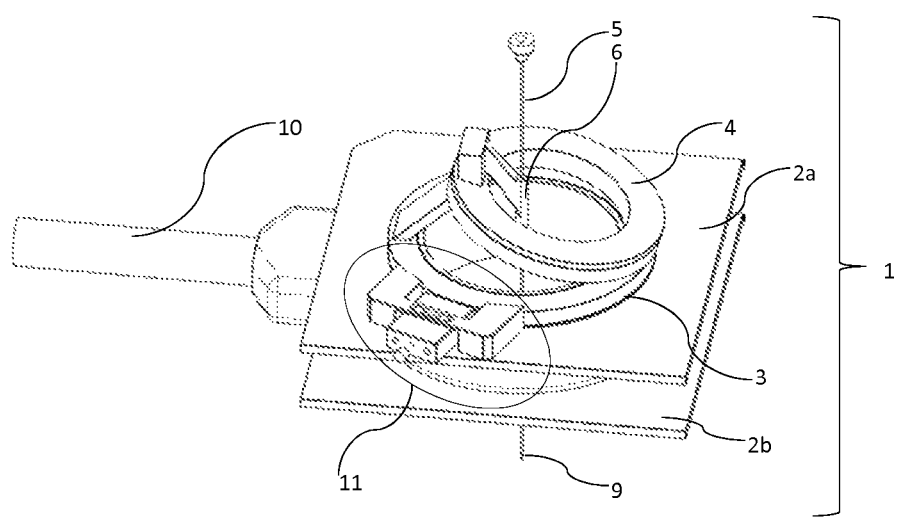
FIG. 10 is a perspective view of another puncture support apparatus according to the third embodiment including a different friction applying mechanism.

FIG. 10 is a perspective view illustrating a state in which the external appearance of the puncture support apparatus 1 having a different friction applying mechanism 11 in the third embodiment is viewed from above. The friction applying mechanism 11 includes a movable member 26 configured to be movable by minutely small amounts after application of friction.

Figure 11A:
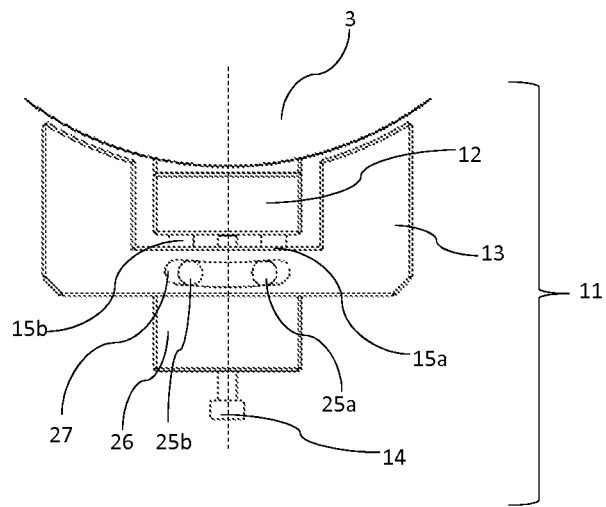
FIG. 11A is a diagram of a friction applying mechanism serving as a modification as viewed from the top.
Figure 11B:
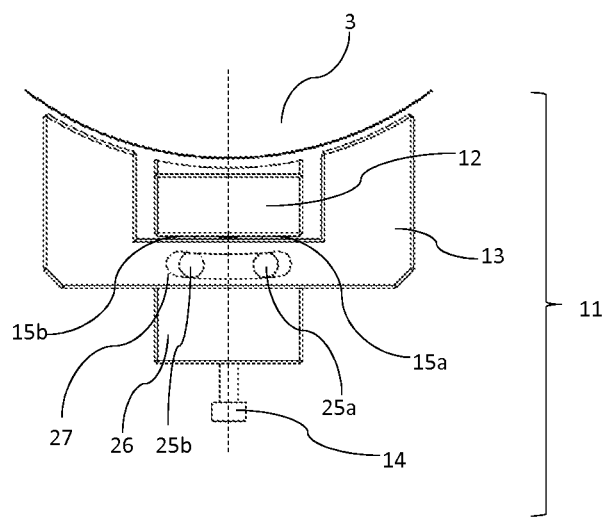
FIG. 11B is another diagram of the friction applying mechanism serving as a modification as viewed from the top.
Figure 11C:
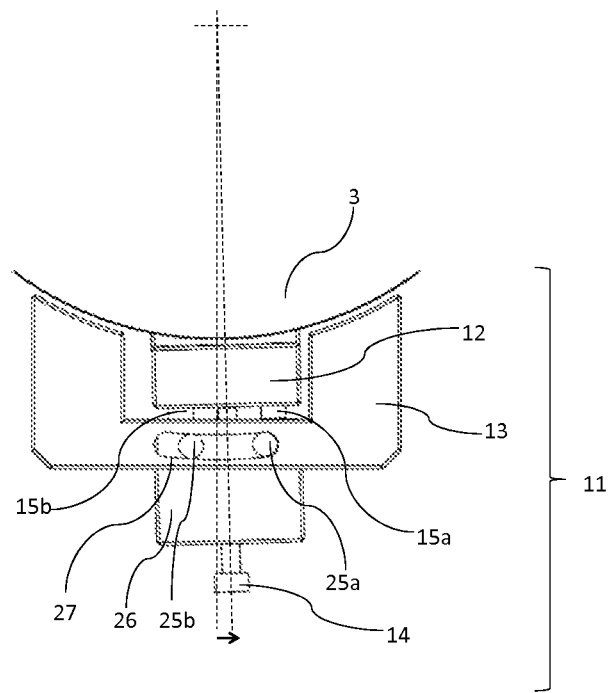
FIG. 11C is another diagram of the friction applying mechanism serving as a modification as viewed from the top.

FIGS. 11A and 11B are diagrams of the friction applying mechanism 11 as viewed from the top. FIG. 11A is a diagram in which the first rotation member 3 is set to a rotation-suppressed state by operating the friction applying mechanism 11, and FIG. 11B is a diagram in which the first rotation member 3 is set to a rotatable state by releasing the friction applying mechanism 11. FIG. 11C is a diagram in which the rotation of the first rotation member 3 is suppressed by operating the friction applying mechanism 11, and also the friction member 12 and movable member 26 are movable by minutely small amounts in the rotation direction of the first rotation member 3. As can be understood by comparing FIGS. 11A and 11B, the friction member holding member 13 movably holds the friction member 12 in the radial direction of the first rotation member 3. Also, though movement has not been permitted regarding the rotation direction (circumferential direction) of the first rotation member 3 in FIGS. 2A and 2B in the first embodiment, the movement is permitted in a predetermined range in the present embodiment. More specifically, positioning pins 25a and 25b provided integrally with the movable member 26 are movable or adjustable by minutely small amounts (a predetermined range) in the same direction as the rotation direction of the first rotation member 3 by a slot 27 provided to the friction member holding member 13, thereby suppressing movement in the radial direction. A material with low friction force is employed as the positioning pins 25a and 25b and slot 27, and a material with high friction force is employed as the first rotation member 3 and friction member 12 to provide difference in friction force to the two slide portions, thereby enabling minute adjustment in the rotation direction after setting the first rotation member 3 to a rotation-suppressed state by operating the friction applying mechanism 11.

Fourth Embodiment

Figure 12:
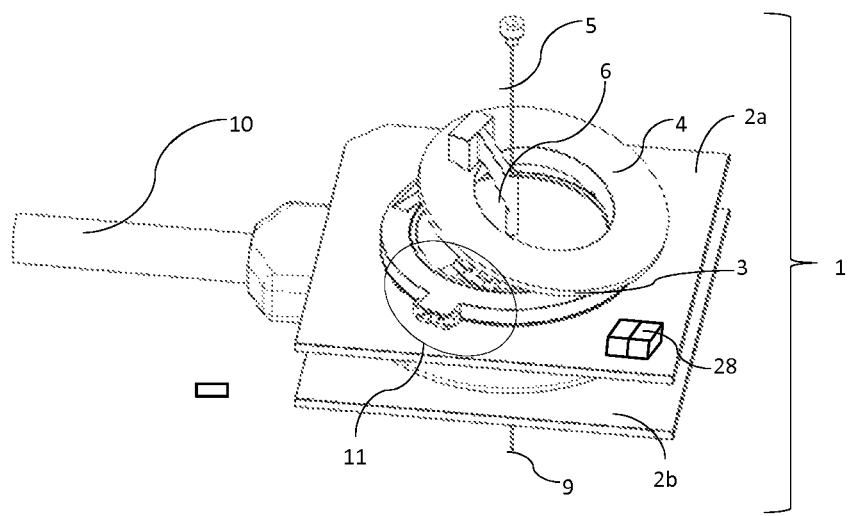
FIG. 12 is a perspective view of a puncture support apparatus according to a fourth embodiment.

FIG. 12 is a perspective view of a puncture support apparatus 1 according to a fourth embodiment, where the display unit 28 is disposed in the base 2a. Also, the friction applying mechanism 11 is installed in the first ring portion 3-1 and second ring portion 3-2 of the first rotation member 3, which serve as friction applying mechanisms corresponding to the first rotation member 3 and second rotation member 4 in the present embodiment, respectively. Also, two of the display units 28 are provided corresponding to the friction applying mechanisms 11. Also, a cover (not illustrated) to prevent the friction member 12 from falling off is attached to the friction applying mechanisms 11. The display units 28 are connected to the friction applying mechanism 11 by a cable (not illustrated), and the status of the friction applying mechanism 11 is displayed on the display units 28.

Figure 13A:
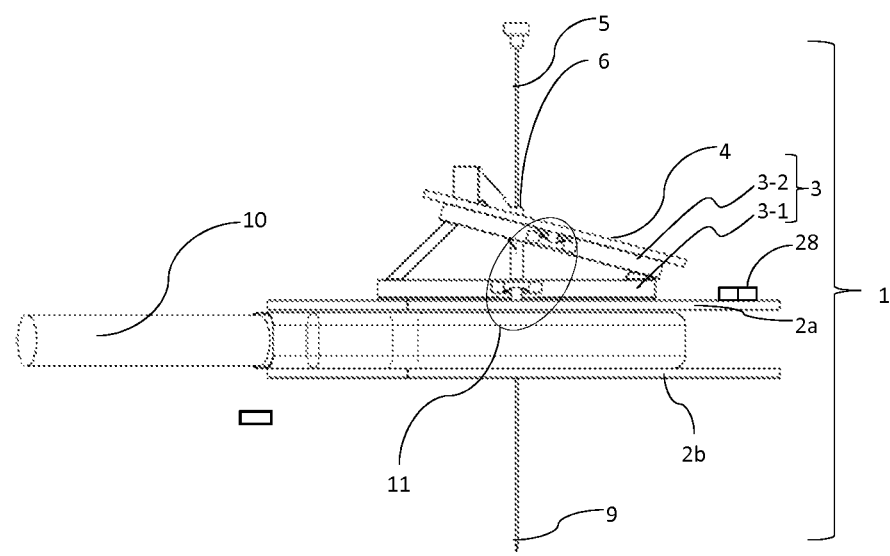
FIG. 13A is a side view of the puncture support apparatus according to the fourth embodiment.
Figure 13B:
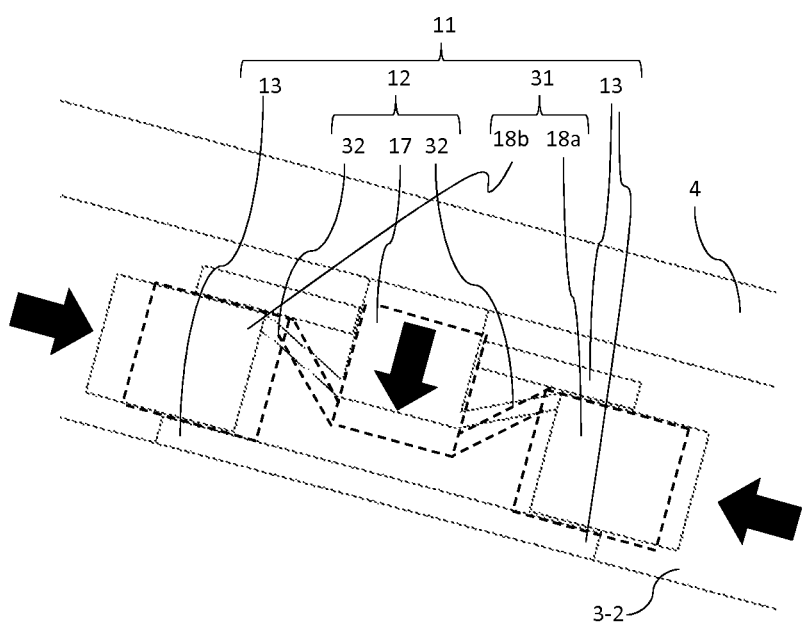
FIG. 13B is a schematic diagram of a friction applying mechanism according to the fourth embodiment.

FIG. 13A is a side view of a puncture support apparatus 1 according to a modification of the fourth embodiment, and FIG. 13B is a schematic diagram of the friction applying mechanism 11 (only the friction applying mechanism 11 configured to perform the rotation suppression of the second rotation member 4). Note that, though FIG. 13A illustrates a mode for directly applying friction force to the second rotation member 4 to cause the second rotation member 4 to generate friction torque, a mode for indirectly applying friction force thereto may be employed. The mode for indirectly applying friction force will be described in detail in later-described FIG. 14. Details of the friction applying mechanism 11 corresponding to the first rotation member 3 are as described in FIGS. 5A and 5B, so detailed description will be omitted here. The outer diameter of the second rotation member 4 protrudes wider than that of the second ring portion 3-2 of the first rotation member 3 which engages with the second rotation member 4, and the friction applying mechanism 11 is formed integrally with the side in the outer diameter of the second ring portion 3-2 of the first rotation member 3.

As illustrated in FIG. 13B, the friction member holding member 13 is provided to the second ring portion 3-2 of the first rotation member 3, where the friction member 12 is fitted thereto. According to the restoring force of the hinge member 32 of the friction member 12, provided as a connection portion between the buttons 18a and 18b, and the friction portion 17, relative force is generated between the friction member holding member 13 and second rotation member 4 to apply friction force between the friction portion 17 and second rotation member 4 for restraining the rotation direction. Thus, the relative rotation of the second rotation member 4 as to the first rotation member 3 is suppressed. Further, the friction portion 17 is separated from the contact surface with the second rotation member 4 by pressing the buttons 18a and 18b of the friction member 12 in the arrow direction in FIG. 13B to deform the hinge portion 32, thereby enabling the second rotation member 4 to be rotatable as to the first rotation member 3.

Figure 14:
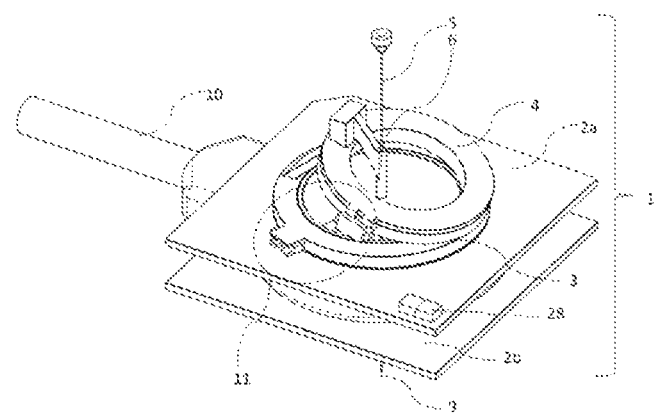
FIG. 14 is a perspective view of another puncture support apparatus according to the fourth embodiment.

FIG. 14 is a perspective view of a puncture support apparatus 1 according to another modification of the fourth embodiment. The friction applying mechanism 11 is installed in the first rotation member 3 and second rotation member 4 in the present modification, which performs suppression of the rotations of the first rotation member 3 and second rotation member 4, respectively. Two of the display units 28 are also provided corresponding thereto. Also, a cover (not illustrated) to prevent the friction member 12 from falling off is attached to the friction applying mechanism 11. The display units 28 are connected to the friction applying mechanism 11 by a cable (not illustrated), whereby the status of the friction applying mechanism 11 is displayed on the display units 28.

Figure 15A:
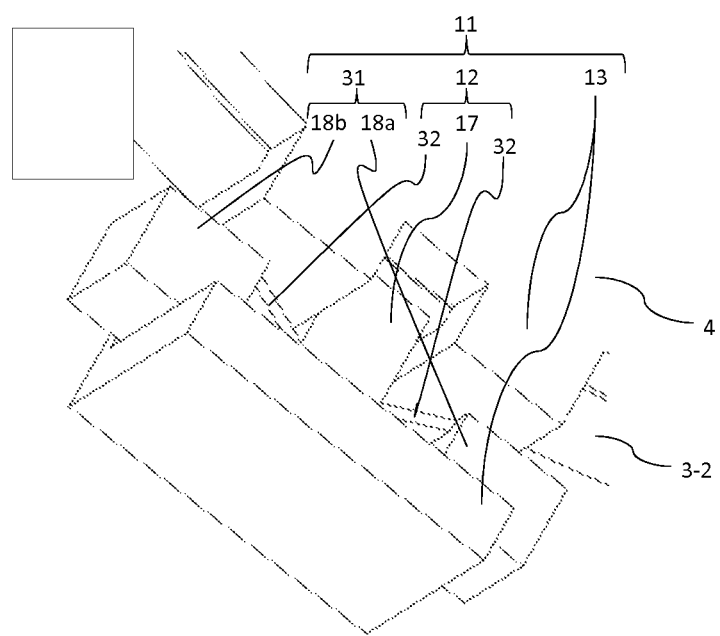
FIG. 15A is a detailed diagram of the friction applying mechanism according to the fourth embodiment.
Figure 15B:
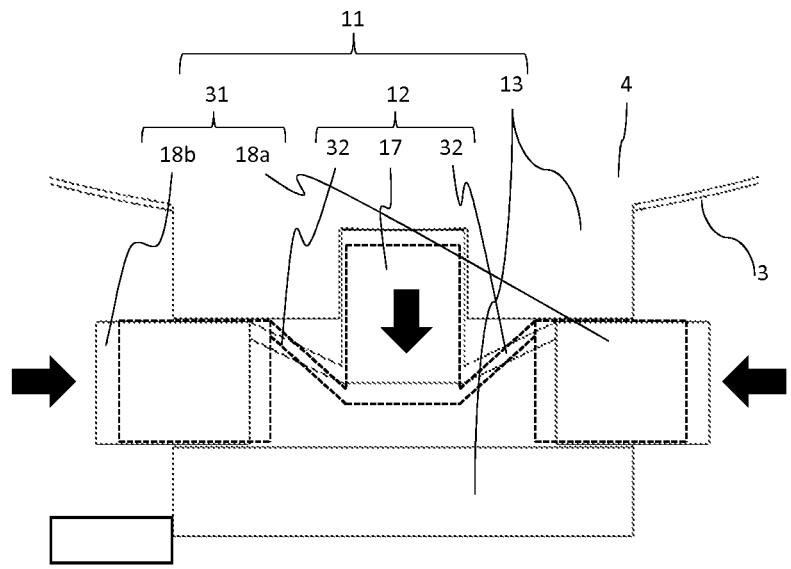
FIG. 15B is a schematic diagram of the friction applying mechanism according to the fourth embodiment.

FIG. 15A is a detailed diagram of a friction applying mechanism 11 according to another modification of the fourth embodiment, and FIG. 15B is a schematic diagram of the friction applying mechanism 11 (only the friction applying mechanism 11 configured to perform the rotation suppression of the second rotation member 4 is illustrated). The friction applying mechanism 11 is formed integrally with the second rotation member 4 in the present modification. The friction member 12 comes into contact with the outer diameter side of the second ring portion 3-2 of the first rotation member 3 to suppress this to the rotation center direction of the second rotation member 4, thereby suppressing the rotation. The friction applying mechanism 11 is operated by the operator, thereby releasing the second rotation member 4 from the friction member 12 which presses the second ring portion 3-2 side of the first rotation member 3 to enable the rotation member 4 to be rotatable. Therefore, the operator can perform releasing of friction force, positioning, and fixing regarding both of the first rotation member 3 and second rotation member 4 by one hand as a series of operations, and consequently, workability is improved.

Further, the present embodiment also enables the elastic storing force of the hinge portions 32 of the two friction applying mechanisms 11 to be set such that the torque component of the friction torque of the second rotation member 4 on the rotation axis of the first rotation member 3 exceeds the torque component of the friction torque of the first rotation member 3 when the two friction applying mechanisms 11 are in a pressing state. Thus, the first rotation member 3 can be rotated by only the manual operations of the second rotation member 4.

Other Embodiments

Figure 16:
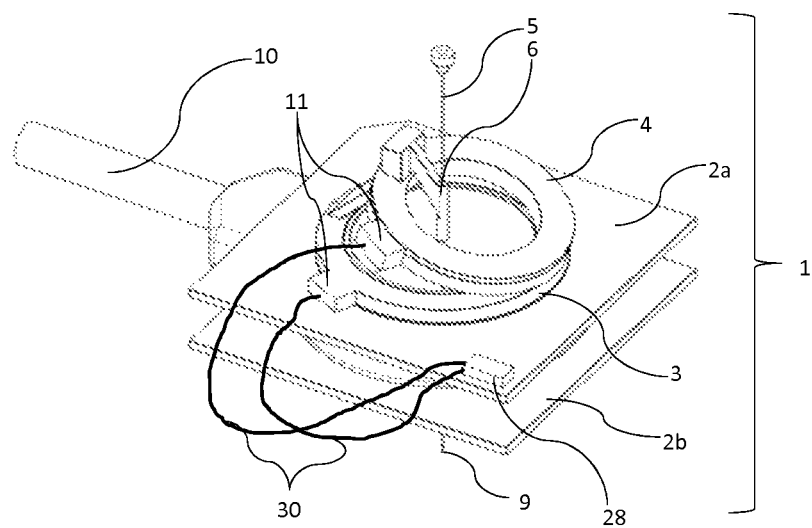
FIG. 16 is a perspective view of a puncture support apparatus according to another embodiment.

FIG. 16 is a perspective view of a puncture support apparatus 1 according to another embodiment. More specifically, FIG. 16 is a perspective view of the puncture support apparatus 1 in which a configuration for disposing the display unit 28 and/or the operation unit in a position far away from the friction applying mechanism 11 is illustrated. A cable 30 extended from the friction applying mechanism 11 is connected to the display unit 28 disposed in the base 2a. A wire (not illustrated) for operating the friction applying mechanism 11 is disposed in the cable 30. The display unit 28 may also be detached from the base 2a for remote operations.

Figure 17:
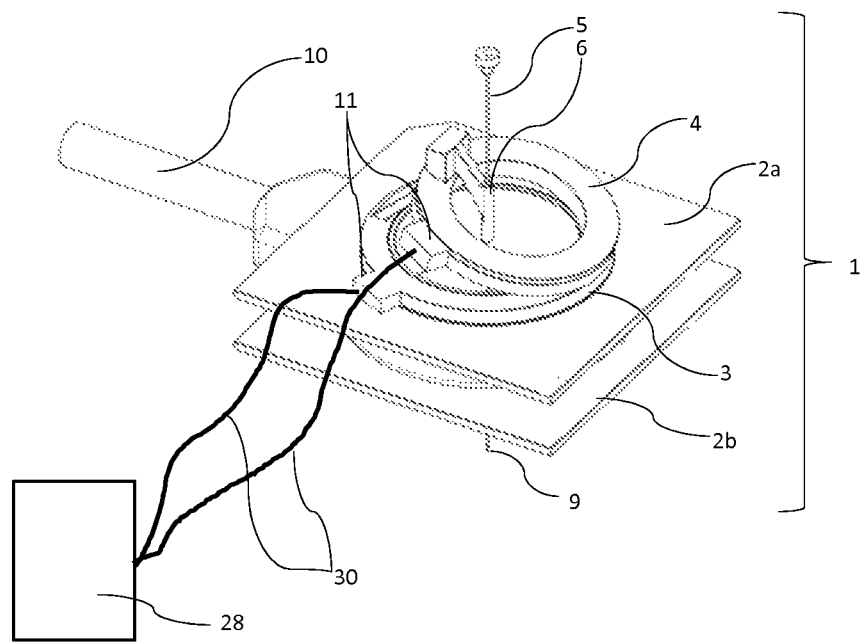
FIG. 17 is a perspective view of another puncture support apparatus according to another embodiment.

FIG. 17 is a perspective view of a puncture support apparatus 1 according to yet another modification, in which the cable 30 extending from the friction applying mechanism 11 is connected to the display unit 28. An optical fiber or line (not illustrated) configured to transmit the status of the friction applying mechanism 11 is disposed in the cable 30. Since the present modification enables detection of the status of the friction applying mechanism 11 at a remote location from the puncture support apparatus 1 and the operator thereof, housing the display unit 28 in a display device of another controller enables this device to serve as part of a medical system, or to serve as another display unit for audio or the like. Further, in the case of providing an encoder which is a position detecting unit within the first rotation member 3 and second rotation member 4, an optical fiber or line configured to transmit position detected signals of these is housed in the cable 30, whereby the status of the friction applying mechanism 11 and also rotation angle information of each rotation member can be provided to the display unit 28.

Also, the first rotation member 3 and second rotation member 4 may include a driving source 31 as another modification. The driving source 31 is connected to the first rotation member 3 and second rotation member 4 via a transmission mechanism which is not illustrated, whereby the movable portions of the first and second rotation members are driven by the driving source 31. This driving mechanism can be realized using, for example, a gear, timing belt, or the like. Each of the first and second rotation members includes the friction applying mechanism 11 in the same way as the above embodiments. The present modification includes the driving source 31, thereby enabling automatic positioning. However, there may be a case where, in a state in which positioning has been completed and the rotation members are stopped, the rotation members are finely adjusted by hand, or a case where the operator himself/herself determines positioning to operate the rotation members by hand. It is difficult for the operator to externally operate the holding force of a motor serving as the driving source 31 at the time of normal stopping. Therefore, providing the friction applying mechanism 11 according to the present modification enables the above problem to be solved even in a support apparatus including a driving device.

Fifth Embodiment

Figure 19:
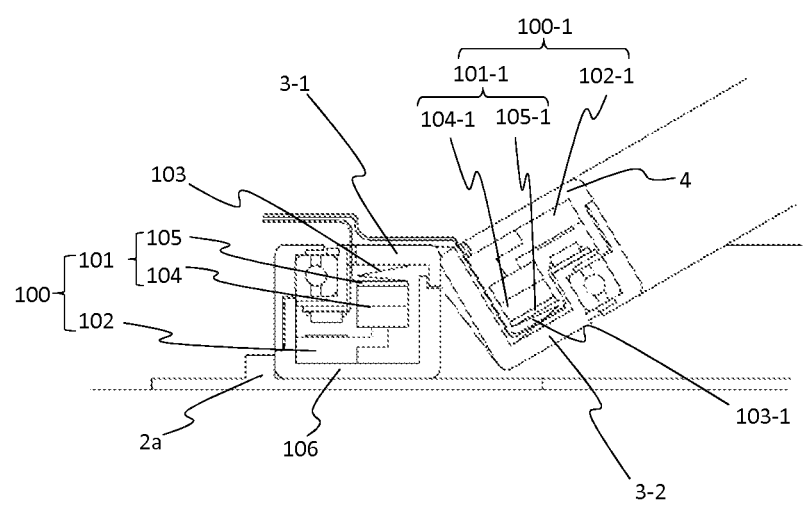
FIG. 19 illustrates a detailed cross-section view of the circle portion showed on the left side in FIG. 18.

In FIG. 19, each ring-shaped actuator 100 and 101 driven by vibration is built inside each rotation member 3 and 4 as the friction applying unit 11. The details will be described below.

The actuator 100 comprises a vibrator 101, a slider 102 which contacts with the vibrator 101 and a pressurizing member 103. The pressurizing member 103 presses the vibrator 101 and may be integrally formed with the ring portion 3-1. The vibrator 101 comprises a vibrator body 104 made by an elastic material and a piezoelectric element 105 adhered to the vibrator body 104. The vibrator 101 is pressurized to the slider 102 by pressurizing member 103. Note that a structure and function of the actuator 100-1 and the pressurizing member 103-1 are basically the same as those described on the actuator 100 and the pressurizing member 103.

The slider 102 is fixed to a case 106. The case 106 is fixed on the base 2a. The slider 102 is indirectly fixed to the base 2a (a first base) through the case 106. The slider 102 may be integrally formed with the case 106. Also the case 106 may be integrally formed with the base 2a. The same thing can be said about the relationship between the slider 102-1 and the rotation member 4. The vibrator 101 is connected to the rotation member 3 (the ring portion 3-1) through the pressurizing member 103 so as to restrict relative rotational movement between the vibrator 101 and the rotation member 3 (the ring portion 3-1). On the right side in FIG. 19, the vibrator 101-1 and the pressurizing member 103-1 are fixed to the ring portion 3-2. The pressurizing member 103-1 may be integrally formed with the ring portion 3-2. Also, the ring portion 3-2 is fixed to the ring portion 3-1 or is integrally formed with the ring portion 3-1. The vibrator 101-1 is fixed to the ring portion 3-2 (that corresponds to the second base) through the pressurizing member 103-1 so as to restrict relative rotational movement between the vibrator 101-1 and the ring portion 3-2.

Friction force in rotational direction of the rotation member 3 (the ring portion 3-1) is generated between the slider 102 and vibrator 101 according to the pressurizing force of the pressurizing member 103. Therefore, the vibrator 101 and pressurizing member 103 work as a friction applying mechanism which generates friction force indirectly between the ring portion 3-1 and the base 2a through the slider 102 and the case 106. Also, it can be say that the slider 102 works as a friction applying mechanism which generates the friction force indirectly between the ring portion 3-1 and the base 2a through the case 106, the vibrator 101 and the pressurizing member 103.

In this embodiment, the frictional torque of the first rotation member 3 (the ring portion 3-1) obtained based on multiplying the frictional force generated between the slider 102 and the vibrator 101 by the radius defined the contacting portion of the vibrator 101 and the slider 102 is greater than the component of friction torque of the second rotation member 4 around the axis of the first rotation member. The component of friction torque of the second rotation member 4 is obtained based on multiplying the friction force generated between the slider 102-1 and the vibrator 101-1 by the radius defined the contacting portion of the vibrator 101-1 and the slider 102-1. Therefore, operator can rotate only the second rotation member by handling only the second rotation member without unexpected rotation of first rotation member 3.

Other Embodiment Relates to the Fifth (Reducing Torque by Vibration)

The friction force of the actuator 101 and 101-1 generated by pressure between vibrator body 104 and 104-1 and slider 102 and 102-1 can be changed by oscillating the vibrator 101 and 101-1 with the specific vibration.

The mechanism of generating the friction between the vibrator body 104 and the slider 102 is explained hereinafter, the mechanism on the vibrator body 104-1 and the slider 102-1 is the basically the same. Applying alternate voltages to the piezoelectric element 105 through electric cables, the vibrator vibrates and generates progressive wave which runs around the ring shaped vibrator body 104. The slider 102 which contact with the vibrator body 104 is driven by the progressive wave generated on the contact surface of the vibrator body 104. The driving force is made by the friction between the slider 102 and the vibrator body 104. Thus, the rotation member 3 (the ring portion 3-1) is electrically rotated by the vibration driven actuator 100.

Also, the friction torque can be changed by generating standing wave on the vibrator body 104. This is another specific vibration. In case of the progressive wave type actuator as described above, the standing wave can be generated by applying alternating voltages with same phase or only one alternating voltage to the piezoelectric element 105. Varying the voltage applied to the piezoelectric element 105, the friction torque can be changed.

Figure 18:
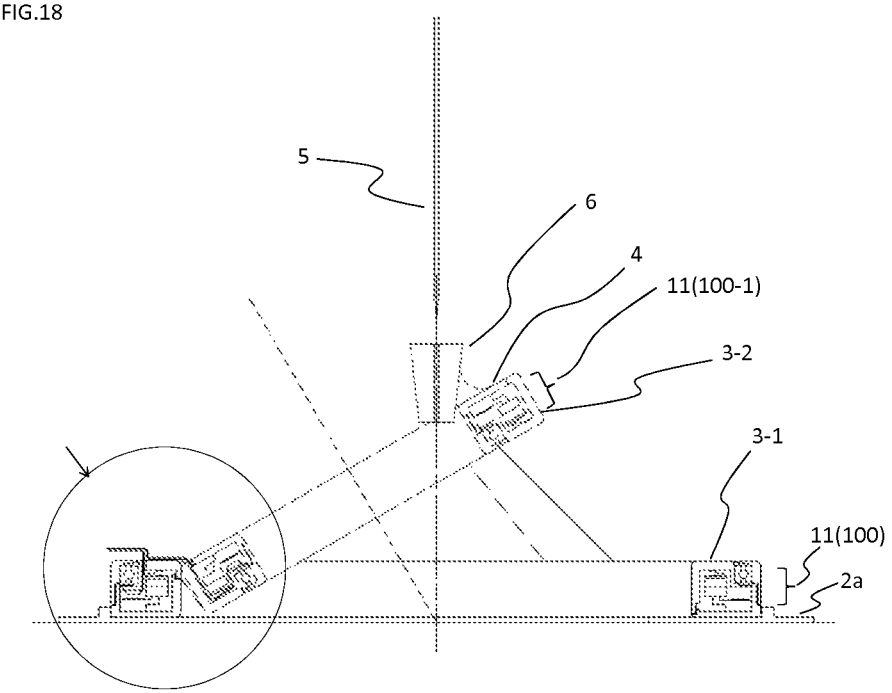
FIG. 18 is a cross-section view of the puncture support apparatus (positioning apparatus) 1 in the fifth embodiment.

The embodiment showed in FIG. 18 and FIG. 19, the puncture support apparatus can be electrically driven/moved by the one ore more actuator(s) which built inside each of the first and the second rotation members 3 and 4. When manual adjustment is needed, each actuator works as the friction applying unit which generates an adjustable friction torque in each rotatable member by changing applying voltages to the piezoelectric element 105 and/or 105-1.

Thus, the positioning adjustment or the movement for positioning of the first rotation member 3 and the second rotation member 4 are performed either electrically or manually with the same mechanical structure.

The actuators described in this embodiment are not limited to the ring-shaped progressive wave type actuators. Actuators of any other vibration types can be used, for example, combination of bending, shearing, shrinking and expansion vibration known as piezoelectric actuators. A vibration source is also not limited to the piezoelectric material. Other Electro-strictive materials, magneto-strictive materials or electro-magnetic components are also applicable.

Although, in the descriptions above, the slider 102 is connected to the case 106 and the pressurizing member 103 is connected to the ring portion 3-1, and the slider 102-1 is connected to the rotation member 4 and the pressurizing member 103-1 is connected to the ring portion 3-2, the present embodiment is not limited to these. The arrangement among the slider 102, the vibrator 101 and the pressurizing member 103 may be upside down. In FIG. 19, the pressurizing member 103 may be fixed to the case 106 and the slider 102 may be fixed to the ring portion 3-1. The pressurizing member 103 may be integrally formed with the case 106 and the slider 102 may be integrally formed with the ring portion 3-1. Also, the pressurizing member 103-1 may be connected to the rotation member 4 and the slider 102-1 may be connected to the ring portion 3-2. The pressurizing member 103-1 may be integrally formed with the rotation member 4 and the slider 102-1 may be integrally formed with the ring portion 3-2.

The arrangement among the slider 102, the vibrator 101 and the pressurizing member 103 may be further changed. Although, in FIG. 19, the pressurizing member 103 and 103-1 are fixed to the vibrator 100 and 101, the present embodiment is not limited to this. The arrangement of the vibrator 101 and the slider 102 that described above may be switched. So does the arrangement of the vibrator 101-1 and the slider 102-1.

For example, in FIG. 19, the pressurizing member 103 may be fixed to the case 106 and the slider 102 may be fixed to the pressurizing member 103. The vibrator 101 may be fixed to the first ring portion 3-1 restricting rotational and axial movement between the vibrator 101 and the ring portion 3-1. In this arrangement, the slider 102 is pressed to the vibrator 101 by the pressurizing member 103. Also, the pressurizing member 103-1 may be fixed to the second rotation member 4 and the slider 102-1 may be fixed to the pressurizing member 103-1. The vibrator 101-1 may be fixed to the ring portion 3-2 restricting rotational and axial movement between the vibrator 101-1 and the ring portion 3-2. In this arrangement, slider 102-1 is pressed to the vibrator 101-1 by the pressurizing member 101-1.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A positioning apparatus comprising:
   a first rotation member having a first rotation flexibility;
   a guide configured to guide needle-shaped medical equipment;
   a second rotation member, which is connected to the first rotation member, including the guide, and having a second rotation flexibility, of which the rotation axis is not parallel to the rotation axis of the first rotation member; and
   a friction applying unit configured to apply friction force to the first rotation member directly or indirectly for causing the first rotation member to generate a friction torque;
   wherein the friction applying unit applies friction force to the first rotation member directly or indirectly so that the first rotation flexibility of the friction torque of the first rotation member is greater than the first rotation flexibility of friction torque to be generated based on the rotation of the second rotation member.

2. The positioning apparatus according to claim 1, wherein the friction applying unit is disposed in a first base configured to support the first rotation member, and applies friction force to the first rotation member, or disposed in the first rotation member, and applies friction force to the first base.

3. The positioning apparatus according to claim 2, wherein the friction applying unit includes
a friction member, and
a pressing portion configured to press the friction member;
and wherein the friction member is moved by pressure by the pressing portion, and comes into contact with the first rotation member or the first base serving as a contact surface to apply friction force thereto.

4. The positioning apparatus according to claim 3, further comprising:
a cam;
wherein the pressing portion is pressed by the cam to move the friction member.

5. The positioning apparatus according to claim 4, wherein a lever is provided to the pressing portion;
and wherein when the lever is rotated with the axis of the pressing portion as the center, the cam presses the pressing portion via the lever to move the friction member.

6. The positioning apparatus according to claim 3, wherein the friction member includes an elastic member having spring properties;
wherein the pressing portion includes an operation unit configured to externally change the magnitude of force to be applied to the elastic member;
and wherein force is transmitted to the elastic member via the operation unit, the elastic member is deformed by displacement of the operation unit, and contact force by the friction member to the contact surface is changed.

7. The positioning apparatus according to claim 6, wherein the operation unit is formed integrally with the friction member.

8. The positioning apparatus according to claim 3, wherein the friction applying unit includes
a holding member configured to hold the friction member movably in the diameter direction of the first rotation member;
and wherein the holding member includes
an adjusting unit configured to enable the friction member to be moved in a predetermined range in the same direction as the rotation direction of the first rotation member.

9. The positioning apparatus according to claim 2 further comprising:
(i) a vibrator that includes an electro-mechanical energy conversion element,
(ii) a slider contacting the vibrator,
(iii) pressurizing member which generates pressing force on a contact surface between the slider and the vibrator, the slider being driven by wave generated on a contact surface of the vibrator when the electro-mechanical energy conversion element performs,
wherein the pressing member is fixed to the first base or the first rotation member and presses the vibrator or slider, and the slider or the vibrator works as the friction applying unit.

10. The positioning apparatus according to claim 9, wherein at least one alternate signal is applied to the electro-mechanical energy conversion element and oscillates the vibrator, wherein the friction force is changeable according to the wave.

11. The positioning apparatus according to claim 2 further comprising a slider that is fixed to the first base or is integrally formed with the first base, wherein the first rotation member comprises:
(i) a vibrator that includes an electro-mechanical energy conversion element and (ii) a pressurizing member that presses the vibrator, the slider being driven by wave generated on a contact surface of the vibrator when the electro-mechanical energy conversion element performs, wherein the slider or the vibrator works as the friction applying unit.

12. The positioning apparatus according to claim 11, wherein at least one alternate signal is applied to the electro-mechanical energy conversion element and oscillates the vibrator wherein the friction force is changeable according to the at least one alternate signal.

13. The positioning apparatus according to claim 2 further comprising
(i) a vibrator that includes an electro-mechanical energy conversion element and
(ii) a pressurizing member that presses the vibrator that is fixed to the first base or is integrally formed with the first base, wherein the first rotation member comprises a slider the slider being driven by wave generated on a contact surface of the vibrator when the electro-mechanical energy conversion element performs, wherein the slider or the vibrator works as the friction applying unit.

14. The positioning apparatus according to claim 13, wherein at least one alternate signal is applied to the electro-mechanical energy conversion element and oscillates the vibrator wherein the friction force is changeable according to the at least one alternate signal.

15. The positioning apparatus according to claim 1, further comprising:
a second friction applying unit configured to apply friction force to the second rotation member directly or indirectly for causing the second rotation member to generate friction torque;
wherein the second friction applying unit is disposed in the second rotation member or a second base configured to support the second rotation member;
and wherein the second friction applying unit disposed in the second rotation member applies friction force to the second base, and the second friction applying unit disposed in the second base applies the friction force to the second rotation member.

16. The positioning apparatus according to claim 15 further comprising
(i) a vibrator that includes an electro-mechanical energy conversion element
(ii) a slider contacting the vibrator
(iii) pressurizing member which generates pressing force on a contact surface between the slider and the vibrator, the slider being driven by wave generated on a contact surface of the vibrator when the electro-mechanical energy conversion element performs,
wherein the pressing member is fixed to the second base or the second rotation member and presses the vibrator or slider, and the slider or the vibrator works as the friction applying unit.

17. The positioning apparatus according to claim 16, wherein at least one alternate signal is applied to the electro-mechanical energy conversion element and oscillates the vibrator wherein the friction force is changeable according to the at least one alternate signal.

18. The positioning apparatus according to claim 15 further comprising
(i) a vibrator that includes an electro-mechanical energy conversion element and
(ii) a pressurizing member that presses the vibrator that is fixed to the second base or is integrally formed with the second base, wherein the second rotation member comprises a slider, the slider being driven by wave generated on a contact surface of the vibrator when the electro-mechanical energy conversion element performs, wherein the slider or the vibrator works as the friction applying unit.

19. The positioning apparatus according to claim 18, wherein at least one alternate signal is applied to the electro-mechanical energy conversion element and oscillates the vibrator wherein the friction force is changeable according to the at least one alternate signal.

20. The positioning apparatus according to claim 15 further comprising a slider that is fixed to the second base or is integrally formed with the second base, wherein the second rotation member comprises
(i) a vibrator that includes an electro-mechanical energy conversion element and
(ii) a pressurizing member that presses the vibrator, the slider being driven by wave generated on a contact surface of the vibrator when the electro-mechanical energy conversion element performs, wherein the slider or vibrator works as the friction applying unit.

21. The positioning apparatus according to claim 20, wherein at least one alternate signal is applied to the electro-mechanical energy conversion element and oscillates the vibrator wherein the friction force is changeable according to the at least one alternate signal.

22. The positioning apparatus according to claim 1, further comprising:
a notification part configured to notify whether or not the friction applying unit has applied friction force.

23. The positioning apparatus according to claim 1, further comprising:
a remote operation unit configured to operate the friction applying unit from remote.

* * * * *